United States Patent [19]

Vince et al.

[11] Patent Number: 5,122,517

[45] Date of Patent: Jun. 16, 1992

[54] ANTIVIRAL COMBINATION COMPRISING NUCLEOSIDE ANALOGS

[75] Inventors: Robert Vince, St. Paul, Minn.; William M. Shannon, Vestavia Hills, Ala.

[73] Assignee: Regents of the University of Minnesota, Minneapolis, Minn.

[21] Appl. No.: 611,322

[22] Filed: Nov. 13, 1990

Related U.S. Application Data

[63] Continuation of Ser. No. 357,137, May 30, 1989, abandoned, which is a continuation-in-part of Ser. No. 205,163, Jun. 10, 1988, abandoned.

[51] Int. Cl.$^5$ .............................................. A61K 48/00
[52] U.S. Cl. ........................................ 514/50; 514/45; 514/46; 514/49; 514/50; 514/258; 514/262; 514/265; 514/885
[58] Field of Search ................ 514/49, 50, 258, 265, 514/885, 45, 46, 262

[56] References Cited

U.S. PATENT DOCUMENTS

| | | | |
|---|---|---|---|
| 4,724,232 | 2/1988 | Rideout et al. | 514/50 |
| 4,880,782 | 11/1989 | Eckstein et al. | 514/45 |
| 4,916,122 | 4/1990 | Chu et al. | |
| 4,916,224 | 4/1990 | Vince et al. | 514/265 |
| 4,931,559 | 6/1990 | Vince | |
| 4,950,758 | 8/1990 | Vince | |
| 4,999,428 | 3/1991 | Saksena et al. | |

FOREIGN PATENT DOCUMENTS

| | | |
|---|---|---|
| 159264 | 10/1985 | European Pat. Off. |
| 215759 | 3/1987 | European Pat. Off. |
| 2574407 | 6/1986 | France |

OTHER PUBLICATIONS

Drugs: vol. 34, pp. 372–390, "Antiviral Therapy in AIDS", Sandstrom et al., 1987.
Yarchoan et al., NEJM: vol. 36: pp. 557–564, Feb. 26, 1987.
M. A. Fischl et al., *New Engl. J. Med.*, 317, 185 (1987).
P. Herdewijn et al., *J. Med. Chem.*, 31, 2040 (1988).
R. Vince et al., an Abstract in *Antiviral Research*, 9 (1), 120 (1988).
E. L. White et al., *Biochem. Biophys. Res. Comm.*, 161, 393 (1989).
M. W. Vogt et al., *Science*, 235, 1376 (1987).
H. Mitsuya et al., *PNAS USA*, 84, 2033 (1987).

*Primary Examiner*—John W. Rollins
*Assistant Examiner*—James O. Wilson
*Attorney, Agent, or Firm*—Merchant, Gould, Smith, Edell, Welter & Schmidt

[57] ABSTRACT

Antiviral and antitumor compositions are disclosed comprising a mixture of AZT, ribavirin, d4T or CS-87 with a compound of general formula:

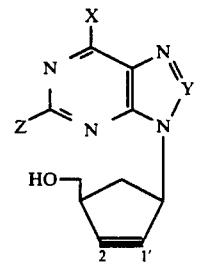

wherein Z is H, OH or NH$_2$, Y is CH, and X is selected from the group consisting of H, N(R)$_2$, SR, OR or halogen, wherein R is H, lower(C$_1$–C$_4$)alkyl, aryl or mixtures thereof, and the pharmaceutically-acceptable derivatives thereof.

9 Claims, 5 Drawing Sheets

ISOBOLOGRAM FOR 50% INHIBITION OF HIV-1 REPLICATION IN CEM CELLS BY (−)14a AND AZT

3b, Z=H, Z'=NH$_2$
4b, Z=NH$_2$, Z'=H
5b, Z=NH$_2$, Z'=-N=N-Ar-pCl
6b, Z=NH$_2$, Z'=NH$_2$

14a [ln (CONCENTRATION ug/ml)]

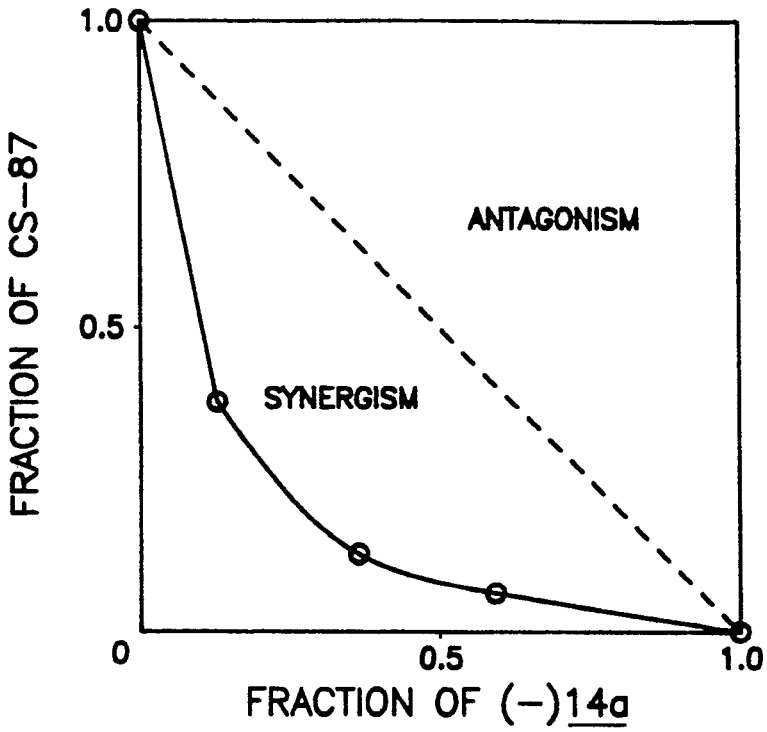
ISOBOLOGRAM FOR 50% INHIBITION OF HIV-1
REPLICATION IN CEM CELLS BY (−)14a AND CS-87
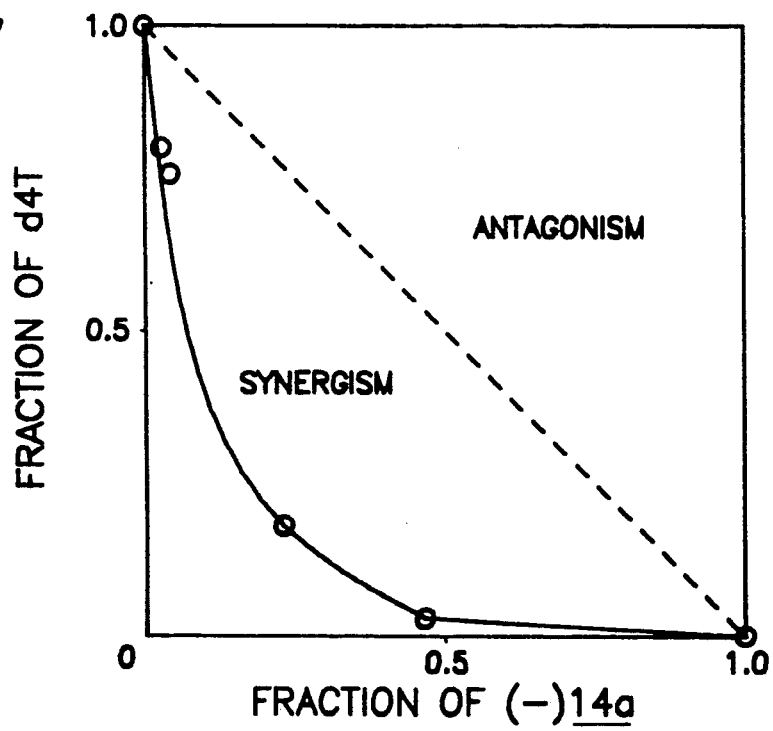
ISOBOLOGRAM FOR 50% INHIBITION OF HIV-1
REPLICATION IN CEM CELLS BY (−)14a AND d4T

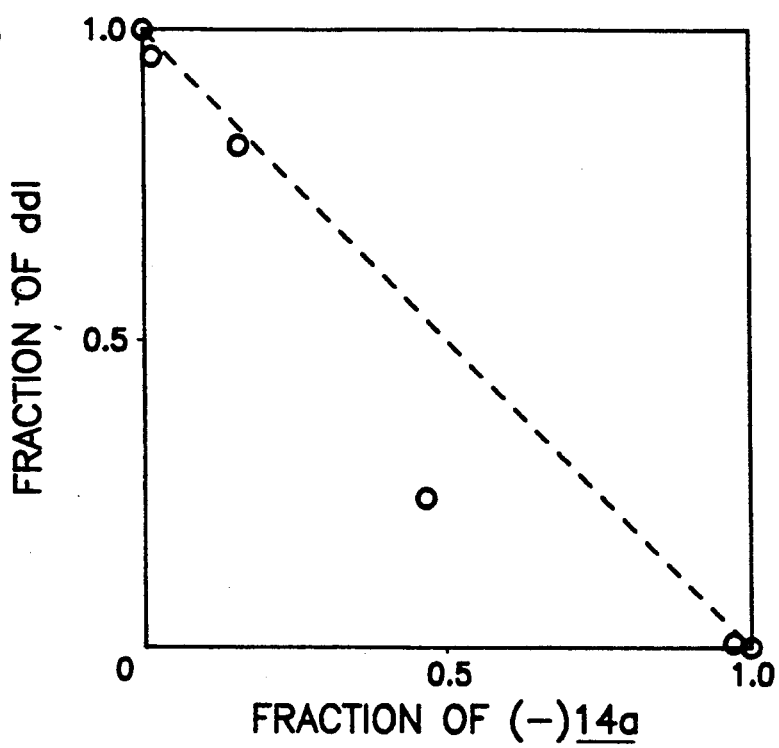
ISOBOLOGRAM FOR 50% INHIBITION OF HIV-1
REPLICATION IN CEM CELLS BY (−)14a AND ddl
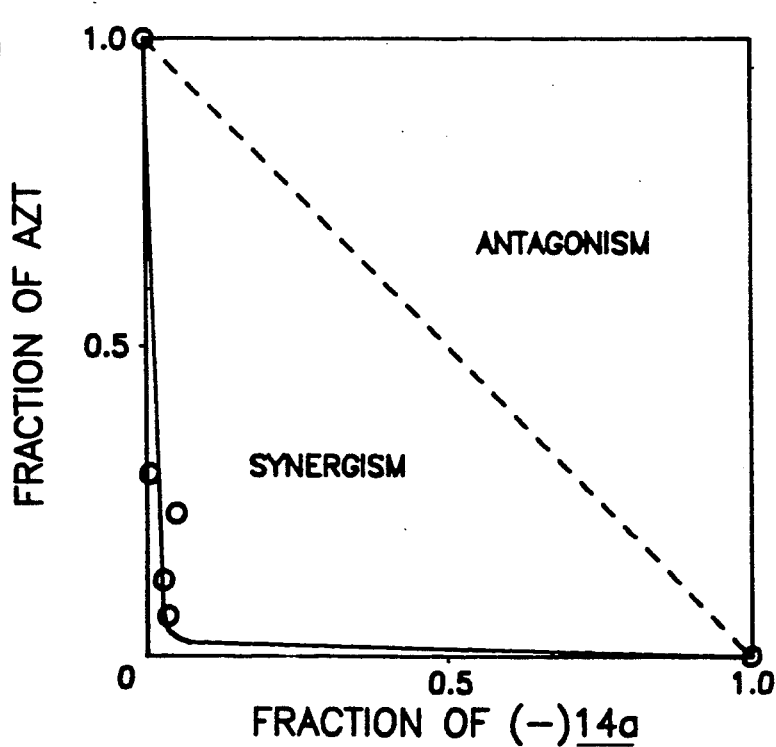
ISOBOLOGRAM FOR 50% INHIBITION OF HIV-1
REPLICATION IN CEM CELLS BY (−)14a AND AZT

ANTIVIRAL COMBINATION COMPRISING NUCLEOSIDE ANALOGS

CROSS-REFERENCE TO RELATED APPLICATION

This is a continuation of application Ser. No. 07/357,137, filed May 30, 1989, which was abandoned upon the filing hereof, which is a continuation-in-part of U.S. application Ser. No. 07/205,163, filed Jun. 10, 1988, now abandoned.

FIELD OF THE INVENTION

The present invention relates to a combination of certain dideoxycarbocyclic nucleosides with the antiviral agents AZT, ribavirin, D4T, DDI, or CS87 which exhibit antiviral activity.

BACKGROUND OF THE INVENTION

Despite intensive effort to discover drugs of value in the systemic treatment of human immunodeficiency virus (HIV) infections, such infections have been singularly resistant to chemotherapy. The intracellular and intimate relation to nuclear metabolism of virus reproduction makes it difficult to destroy a virus without irreparable damage to the host cell.

The discovery of the antiviral activity of vidarabine (9-β-D-arabinofuranosyladenine monohydrate) has led to the preparation of a large number of synthetic nucleosides. To date, only one synthetic nucleoside, 3'-azido-3'-deoxythymidine (AZT) has been approved for treating certain AIDS patients, but it is a palliative, not a cure.

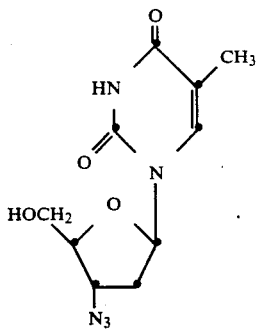

(AZT)

Although AZT is specifically active against retroviruses, its use has led to side effects, including anemia, headache, confusion, anxiety, nausea and insomnia. The AZT analog, 3'-azido-2',3'-dideoxyuridine ("AzddUrd" or "CS-87") has also been found to possess significant activity against HIV in vitro, and is currently in clinical trials to assess its efficacy in the treatment of AIDS. Ribavirin (RIB) has been used to treat viral respiratory infections caused by Rous Sarcoma Virus (RSV) in children. In early clinical trials, it inhibited viral replication and improved immune function in AIDS patients. Long-term studies in patients with AIDS-related complex (ARC) are in progress.

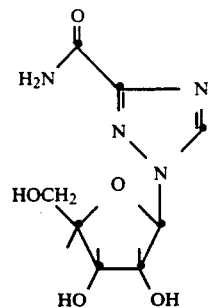

(RIB)

The synthesis of adenine ("6-amino-purine") nucleoside analogues in which the pentose sugar has been replaced with tris(hydroxy)-substituted cyclopentyl residues has yielded compounds with substantial cytotoxic and antiviral activity. For example, the carbocyclic analogue of vidarabine, cyclaradine (Cy), is highly active against Herpes Simplex Virus Type 2 (HSV-2), but exhibits a low therapeutic index (TI$_{50}$=10) against HIV in vitro.

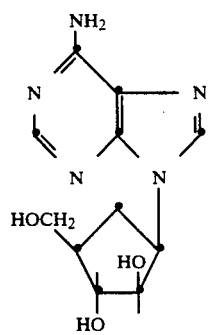

(CY)

T. L. Nagabhushan et al. (U.S. Pat. No. 4,636,383) disclose that a combination of cyclaradine and alpha-interferon exhibits a synergistic increase in potency against HSV-2 infections.

2',3'-Dideoxyinosine ("ddI") has also been shown to possess significant antiviral activity against HIV in vitro.

Vince et al. (U.S. patent application Ser. No. 07/146,262, filed Jan. 20, 1988) disclosed a new class of antiviral and antitumor compounds of general formula: (I).

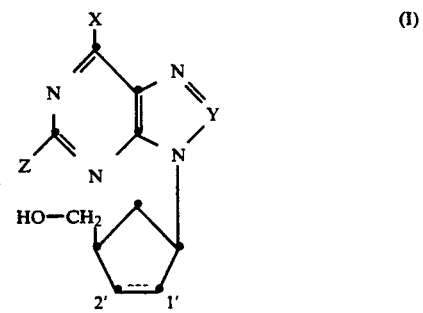

wherein Z is H, OH or NH$_2$, Y is CH or N, the bond indicated by C$_1$'- - - C$_2$' is absent or, in combination with the C$_1$'-C$_2$' bond, is the unit CH=CH and X is selected from the group consisting of H, N(R)$_2$, SR, OR or halogen, wherein R is H, lower (C$_1$-C$_4$)alkyl, aryl or mixtures thereof, and the pharmaceutically-acceptable salts thereof.

Although generally, when used alone, compounds of formula I are not active against Herpes Simplex Virus Type 2 (HSV-2), some of them exhibit specific antiviral activity against other viruses such as HSV-1, human cytomegalovirus (HCMV) and/or retroviruses such as HIV. Specifically, the compound of formula I, wherein X is OH, Z is NH2, Y is CH and the bond—is present, (14a) strongly inhibits HIV infectivity in vitro. However, the carbocyclic analogue of AZT is inactive against HIV, and it is clear that the structure-activity relationships between the variously substituted carbocyclic nucleosides which have been prepared and tested remain ill-defined.

Thus, a substantial need exists for chemotherapeutic agents effective to protect mammalian cells against infection by viruses such as HSV-2, HIV, EBV, varicellazoster vaccinia, human cytomegalovirus (HCMV) and the like.

SUMMARY OF THE INVENTION

The present invention relates to synergistic combinations of carbocyclic antiviral agents with other antiviral agents, to the use of such combinations in therapy and to pharmaceutical formulations comprising combinations of such antiviral agents.

There is therefore provided in a first aspect of the invention a combination of a carbocyclic compound of formula (I):

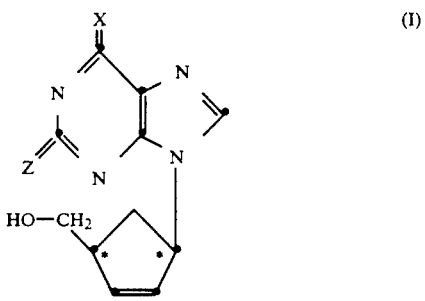

(I)

wherein X is hydrogen, $NRR^1$, SR, OR or halogen; Z is hydrogen, $OR^2$ or $NRR^1$; R, $R^1$ and $R^2$ may be the same or different and are selected from hydrogen, $C_{1-4}$alkyl and aryl; and pharmaceutically-acceptable derivatives thereof, and an antiviral compound selected from AZT, ribavirin, 3'-azido-2',3'-dideoxyuridine ("AzddUrd" or "CS-87") and 2',3'-dideoxy-2',3'-didehydrothymidine ("ddeThd" or "d4T").

It will be appreciated by those skilled in the art that the compounds of formula (I) are cis compounds and further, that the cyclopentene ring of the compounds of formula (I) contain two chiral centres (shown in formula (I) by (*) and may thus exist in the form of two optical isomers (i.e., enantiomers) and mixtures thereof including racemic mixtures. All such isomers and mixtures thereof, including racemic mixtures, are included within the scope of the invention. Thus, in the compounds of formula (I), either the chiral centre to which the base is attached is in the R configuration and the chiral centre to which the CH2OH moiety is attached is in the S configuration (herein-after the D isomer) or the chiral centre to which the base is attached is in the S configuration and that to which the CH2OH moiety is attached is in the R configuration (herein-after the L isomer). Conveniently, the compounds will be in the form of either a racemic mixture or substantially as the pure D isomer. The D isomers may be represented by the formula (Ia):

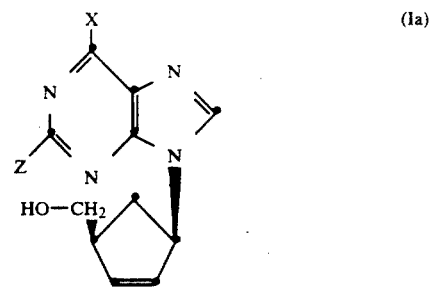

(Ia)

wherein X and Z are as defined for formula (I). Reference hereinafter to compounds of formula (I) include compounds of formula (Ia).

It will also be appreciated by those skilled in the art that certain of the compounds of formula (I) may exist as a number of tautomeric forms and all such tautomers are included within the scope of the invention.

As used herein, the term "halogen" refers to fluorine, chlorine, bromine and iodine; when X is halogen, it is preferably chlorine.

As used herein, $C_{1-4}$alkyl refers to a straight or branched chain alkyl group; for example, methyl, ethyl, n-propyl, iso-propyl, n-butyl, sec-butyl and t-butyl. Conveniently, $C_{1-4}$alkyl is methyl.

As used herein, aryl refers to any mono- or polycyclic aromatic moiety and includes unsubstituted and substituted aryl (such as phenyl, tolyl, xylyl, anisyl) and unsubstituted and substituted aralkyl including ar($C_{1-4}$)alkyl such as phen($C_{1-4}$)alkyl, for example, benzyl or phenethyl In the compounds of formula (I), Z is preferably amino.

In one preferred class of compounds of formula (I), X is OR, in particular, OH.

In a further preferred class of compounds of formula (I), X is $NRR^1$, in particular, NH2, or hydrogen.

Particularly preferred compounds of formula (I) are those wherein Z is NH2 and X is H, NH2 or, especially, OH. Such compounds in particular have especially desirable therapeutic indices as antiviral agents.

By "a pharmaceutically-acceptable derivative" is meant any pharmaceutically-acceptable salt, ester, or salt of such ester, of a compound of formula (I) or any other compound which, upon administration to the recipient, is capable of providing (directly or indirectly) a compound of formula (I) or an antivirally-active metabolite or residue thereof.

Preferred esters of the compounds of formula (I) include carboxylic acid esters in which the non-carbonyl moiety of the ester grouping is selected from hydrogen, straight or branched chain alkyl (e.g., methyl, ethyl, n-propyl, t-butyl, n-butyl), alkoxyalkyl (e.g., methoxymethyl), aralkyl (e.g., benzyl), aryloxyalkyl (e.g., phenoxymethyl), aryl (e.g., phenyl, optionally substituted by halogen, $C_{1-4}$alkyl or $C_{1-4}$alkoxy); sulphonate esters such as alkyl- or aralkylsulphonyl (e.g., methanesulphonyl); amino acid esters (e.g., L-valyl or L-isoleucyl) and mono-, di- or tri-phosphate esters.

With regard to the above-described esters, unless otherwise specified, any alkyl moiety present advantageously contains 1 to 18 carbon atoms, particularly 1 to 4 carbon atoms. Any aryl moiety present in such esters advantageously comprises a phenyl group.

Pharmaceutically-acceptable salts of the compounds of formula (I) include those derived from pharmaceutically-acceptable inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful in the preparation of salts useful as intermediates in obtaining the compounds of the invention and their pharmaceutically-acceptable acid addition salts.

Salts derived from appropriate bases include alkali metal (e.g., sodium), alkaline earth metal (e.g., magnesium), ammonium and $NR_4^+$ (wherein R is $C_{1-4}$alkyl) salts.

References hereinafter to a compound according to the invention includes both compounds of formula (I) and their pharmaceutically-acceptable derivatives.

Specific compounds of formula (I) include:
($1\alpha,4\alpha$)-4-(6-Chloro-9H-purin-9-yl)-2-cyclopentenyl-carbinol;
($1\alpha,4\alpha$)-4-(6-Hydroxy-9H-purin-9-yl)-2-cyclopentenyl-carbinol;
($1\alpha,4\alpha$)-4-(6-Amino-9H-purin-9-yl)-2-cyclopentenyl-carbinol;
($1\alpha,4\alpha$)-4-(6-Mercapto-9H-purin-9-yl)-2-cyclopentenyl-carbinol;
($1\alpha,4\alpha$)-4-(2-Amino-6-chloro-9H-purin-9-yl)-2-cyclopentenyl-carbinol;
($1\alpha,4\alpha$)-4-(2-Amino-6-hydroxy-9H-purin-9-yl)-2-cyclopentenyl-carbinol;
($1\alpha,4\alpha$)-4-(2,6-Diamino-9H-purin-9-yl)-2-cyclopentenyl-carbinol;
in the form of a racemic mixture or a single enantiomer.

The preferred compound of formula (I) for use in the combinations of the present invention is ($1\alpha,4\alpha$)-4-(2-amino-6-hydroxy-9H-purin-9-yl)-2-cyclopentenyl-carbinol, in particular the D isomer thereof as defined herein.

Specifically, the racemic compound of formula (I), wherein X is OH, Z is $NH_2$, and R' is H (14a), strongly inhibits HIV infectivity in vitro. The $TI_{50}$ of this compound varied with the infected cell line which was used to assay for anti-HIV activity, but generally fell between 200–400, and was determined to be as high as 667 in one assay. The 1α-acetate ester of 14a was also active against HIV, giving 28% inhibition at 6 μg/ml. Compound 14a is also active against HSV-1.

The fully resolved D isomer of formula (I), wherein X is OH, Z is $NH_2$, ((−)14a, [(1S,4R)-4-(2-amino-6-hydroxy-9H-purin-9-yl)-2-cyclopentenylcarbinol] is also highly active against HIV. Compounds of formula (I) wherein X is Cl or $NH_2$, Y is CH, Z is $NH_2$ and R' is H (13a and 15a, respectively) are also active against HIV, as are compounds wherein X is Cl, $NH_2$, or SH, Z is H and R' is H (7a, 9a and 10a, respectively). It is believed that the antiviral activity is due to an inhibitory effect on the ability of viruses to infect normal mammalian cells.

The compounds of formula (I) and the second antiviral agents are synergistic over a wide ratio, for example, 1:20 to 20:1, preferably 1:5 to 5:1, particularly about 1:3 to 3:1. Conveniently, each compound will be employed in the combination in an amount at which it exhibits antiviral activity when used alone.

Alkanoyl or (alkoxy)alkanoyl esters of the 3'-(hydroxymethyl) group of either AZT, ribavirin, d4T, CS-87 or the compound of formula (I) can also be used in the present combination, and may lead to an increase in efficacy. For example, see Vince (U.S. Pat. No. 4,362,729), the disclosure of which is incorporated by reference herein, which discloses salts and antiviral alkoxyalkanoate esters of cyclaradine.

Surprisingly, the present combination of the invention exhibits synergistic inhibitory activity against HIV in vitro. In other words, as shown in FIGS. 3–7, a combination of either AZT, ribavirin, CS-87, or d4T, with a preferred compound of formula (I), 14a, exhibited an inhibitory effect against HIV which was substantially greater than the effect of an equivalent amount of either AZT, ribavirin, CS-87, d4T or 14a, used alone. On the other hand, as shown in FIG. 8, combinations of (a) a compound of the formula (I),(−)14a, and (b) ddI did not exhibit similar synergistic antiviral activity against HIV in vitro. This particular combination appears only to be additive in its inhibitory effect against HIV in vitro. Thus, not all anti-HIV agents with confirmed activity against the virus in vitro will exhibit synergistic antiviral activity in combination with a compound of the formula (I). Pyrimidine nucleoside analogs (such as AZT, CS-87 and d4T) are apparently preferable to purine nucleoside analogs (such as ddI) to use in combination with a compound of the formula (I) to achieve synergistic antiviral activity against HIV and related retroviruses.

Combinations of (a) the resolved enantiomer of 14a, (−)14a, with (b) CS-87, d4T, or AZT, as shown in FIGS. 6, 7, and 9, respectively, exhibited significant synergism in their activities against HIV in vitro. Thus, the resolved (−) enantiomer of a compound of the formula (I) is at least as effective as the racemic mixture in producing a synergistic antiviral effect against HIV when combined with these other antiviral agents. The use of the resolved (−) enantiomer of a compound of the formula (I) in antiviral combinations is also within the scope of the invention.

Thus, it is expected that the present combinations will be generally useful against viral infections or virus-associated tumours in humans, and the method of their use to inhibit viral infectivity or tumour growth in vitro or in vivo is also within the scope of the present invention.

Thus, there is provided in a second aspect a method for the treatment of a viral infection in a mammal, including man, comprising co-administration of an antiviral compound of formula (I) and a second antiviral agent selected from AZT, ribavirin, d4T, and CS-87. Therapeutical methods comprising administration of a combination of one or more compounds of formula (I) and more than one of the second antiviral agents, either together or in a plurality of paired combinations, is also within the scope of the invention.

It will be appreciated that the compound of formula (I) and the second antiviral agent may be administered either simultaneously, sequentially or in combination. If administration is sequential, the delay in administering the second of the active ingredients should not be such as to lose the benefit of the synergistic effect of the combination. Preferably, administration will be simultaneous.

It will be appreciated by those skilled in the art that reference herein to treatment extends to prophylaxis as well as the treatment of established infections or symptoms.

It will be further appreciated that the amount of a combination of the invention required for use in treatment will vary not only with the particular compound selected but also with the route of administration, the nature of the condition being treated and the age and condition of the patient and will be ultimately at the discretion of the attendant physician or veterinarian. In general, however, a suitable dose will be in the range of from about 1 to about 750 mg/kg, e.g., from about 10 to about 750 mg/kg of bodyweight per day, such as 3 to about 120 mg per kilogram bodyweight of the recipient per day, preferably, in the range of 6 to 90 mg/kg/day, most preferably in the range of 15 to 60 mg/kg/day of each of the active ingredients of the combination.

The desired dose may conveniently be presented in a single dose or as divided doses administered at appropriate intervals, for example, as two, three, four or more sub-doses per day.

The combination is conveniently administered in unit dosage forms; for example, containing 10 to 1500 mg, conveniently 20 to 1000 mg, most conveniently 50 to 700 mg of each active ingredient per unit dosage form.

Ideally, the combinations should be administered to achieve peak plasma concentrations of each of the active compounds of from about 1 to about 75 $\mu$M, preferably about 2 to 50 $\mu$M, most preferably about 3 to about 30 $\mu$M. This may be achieved, for example, by the intravenous injection of a 0.1 to 5% solution of the active ingredients, optionally in saline, or orally administered as a bolus containing about 1 to about 100 mg of each active ingredient. Desirable blood levels may be maintained by a continuous infusion to provide about 0.01 to about 5.0 mg/kg/hour or by intermittent infusions containing about 0.4 to about 15 mg./kg of each active ingredient.

While it is possible that, for use in therapy, the active ingredients of the combination may be administered as the pure chemical, it is preferable to administer the present combinations as pharmaceutical formulations.

The invention thus further provides a pharmaceutical formulation comprising a compound of formula (I) or a pharmaceutically-acceptable derivative thereof and a second antiviral compound selected from AZT, ribavirin, d4T, and CS-87 together with one or more pharmaceutically-acceptable carriers thereof and, optionally, other therapeutic and/or prophylactic ingredients. The carrier(s) must be "acceptable" in the same of being compatible with the other ingredients of the formulation and not deleterious to the recipient thereof.

Pharmaceutical formulations include those suitable for oral, rectal, nasal, topical (including buccal and sublingual), vaginal or parenteral (including intramuscular, sub-cutaneous and intraveneous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, sachets, or tablets, each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds according to the invention may be formulated ointments, creams or lotions, or as a transdermal patch. Ointments and creams may, for example, be formulated with an aqueous or oily base with the addition of suitable thickening and/or gelling agents. Lotions may be formulated with an aqueous or oily base and will, in general, also contain one or more emulsifying agents, stabilizing agents, dispersing agents, suspending agents, thickening agents, or colouring agents.

Formulations suitable for topical administration in the mouth include lozenges comprising the active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing, in addition to the active ingredient, such carriers as are known in the art to be appropriate.

For intra-nasal administration, the compounds of the invention may be used as a liquid spray or dispersible powder or in the form of drops.

Drops may be formulated with an aqueous or non-aqueous base also comprising one or more dispersing agents, solubilizing agents or suspending agents. Liquid sprays are conveniently delivered from pressurized packs.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridge or, e.g., gelatin or blister packs from which the powder may be administered with the aid of an inhalator or insufflator.

When desired, the above-described formulations adapted to give sustained release of the active ingredient may be employed.

The pharmaceutical compositions according to the invention may also contain other active ingredients such as antimicrobial agents, or preservatives.

BRIEF DESCRIPTION OF THE DRAWINGS

FIG. 6 is an isobologram depicting 50% inhibition of HIV replication in CEM cells by compound (−)14a, AzddUrd (CS-87), and combinations thereof.

FIG. 7 is an isobologram depicting 50% inhibition of HIV replication in CEM cells by compound (−)14a, ddeThd (d4T), and combinations thereof.

FIG. 8 is an isobologram depicting 50% inhibition of HIV replication in CEM cells by compound (−)14a, ddI, and combinations thereof.

FIG. 9 is an isobologram depicting 50% inhibition of HIV replication in CEM cells by (−)14a, AZT, and combinations thereof.

DETAILED DESCRIPTION OF THE INVENTION

Figure 1:
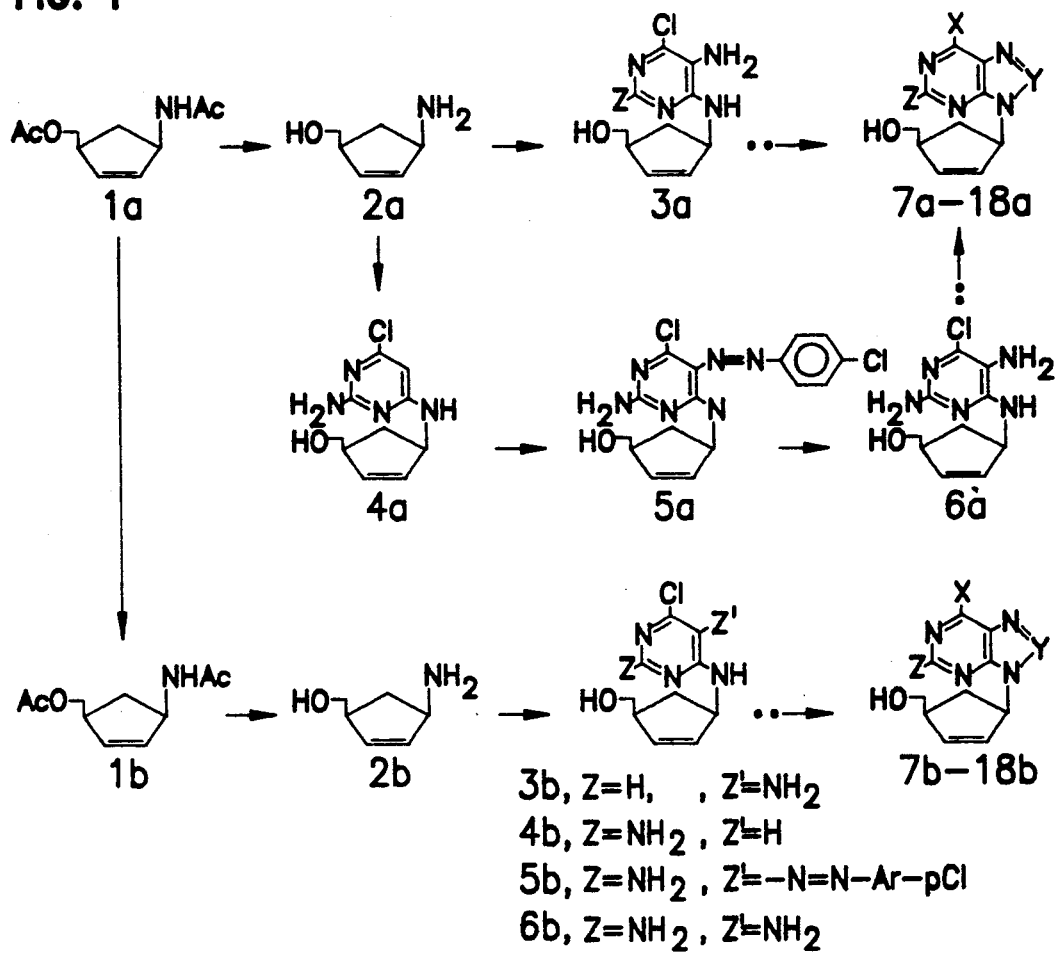
FIG. 1 is a flow diagram summarizing the synthesis of compounds of formula (I).

FIG. 1 outlines the synthesis of preferred compounds of formula from starting material 1a. The structural formulas and some of the properties of compounds 7a–18a are summarized on Table I, below.

TABLE I

| A. 2′,3′-Dideoxy-6-Substituted-Purines of Formula 1, Z = H. | | | | |
|---|---|---|---|---|
| Compound No. | X | M.P. (°C.) | Rf | Yield (%) |
| 7a | Cl | 108–110 | 0.35[a] | 82 |
| 8a | OH | 248–250 (dec) | 0.24[b] | 45 |
| 9a | NH$_2$ | 198–200 | 0.33[b] | 81 |
| 10a | SH | 263–265 (dec) | 0.44[b] | 49 |
| B. 2′,3′-Dideoxy-2,6-Disubstituted-Purines of Formula I, Z = NH$_2$. | | | | |
| Compound No. | X | M.P. (°C.) | Rf[b] | Yield (%) |
| 13a | Cl | 145–147 | 0.64 | 80 |
| 14a | OH | 254–256 (dec) | 0.27 | 61 |
| 15a | NH$_2$ | 152–155 | 0.41 | 80 |

[a]CHCl$_3$:MeOH 10:1.
[b]CHCl$_3$:MeOH, 5:1.

Compounds 7a, 8a, 9a, 10a, 13a, 14a, and 15a are effective to inhibit the infection and killing of human T lymphocytes (T$_h$ cells) by HIV. Likewise, compounds 3a, 3b, 4a, 4b, 5a, 5b, 6a, and 6b, shown on FIG. 1, are effective to inhibit the infection and killing of human T lymphocytes (T$_h$ cells) by HIV. Therefore, in combination with AZT and/or ribavirin, these compounds are candidates for clinical trials in human patients infected with HIV and/or afflicted with AIDS or AIDS-related complex (ARC).

DETAILED DESCRIPTION OF THE INVENTION

Ribavirin

Ribavirin (1-β-D-Ribofuranosyl-1H-1,2,4-triazole-3-carboxamide) was the first synthetic, non-interferon-inducing, broad-spectrum antiviral nucleoside. Its synthesis and bioactivity have been widely reported. For example, see y. Ito et al., *Tetrahedron Letters*, 2521 (1979) and R. R. Schmidt et al., *Ber.*, 114, 2825 (1981) and *Chem. Eng. News*, 28 (Jan. 27, 1986). Ribavirin is commercially available as virazole from ICN Pharmaceuticals, Covina, Calif.

3′-Azido-3′-Deoxythymidine (AZT)

AZT is currently available from Burroughs Wellcome Co., Research Triangle Park, N.C. and has been approved for the treatment of AIDS, ARC and for preventive studies in symptom-free HIV seropositive individuals.

3′-Azido-2′,3′-Dideoxyuridine (AzddUrd; CS-87) has been reported to significantly inhibit HIV replication in vitro. For examples, see Chu et al., *Biochem. Pharmacol.*, 37, 3543 (1988); Lin et al., *J. Med. Chem.*, 31, 336 (1988); and Balzarini et al., *Biochem. Pharmacol.*, 37, 2847 (1988). AzddUrd was made available by Dr. Raymond F. Schinazi (Atlanta, Ga.) and is currently being produced and developed as an anti-HIV drug by Triton Biosciences, Inc. (Alameda, Calif.).

2′,3′-Dideoxy-2′,3′-didehydrothymidine (ddeThd; d4T) has been reported to be a potent inhibitor of HIV replication in vitro. For examples, see Baba et al., *Biochem. Biophys. Res. Commun*, 142, 128 (1987); Lin et al., *Biochem. Pharmacol.*, 36, 2713 (1987); and Hamamoto et al., *Antimicrob. Agents Chemother.*, 31, 907 (1987). The d4T was provided by Glaxo Laboratories (Research Triangle Park, N.C.). This compound is currently being produced and developed as an anti-HIV drug by Bristol-Myers Research Laboratories (Wallingford, Conn.).

2′,3′-Dideoxyinosine (ddI) was first reported to inhibit HIV-induced cytopathic effects in vitro by Mitsuya and Broder, *Proc. Natl. Acad. Sci. USA*, 83, 1911 (1986). The ddI was obtained from Dr. Jack Secrist (Southern Research Institute, Birmingham, Ala.) and is currently being produced and developed as an anti-HIV drug by Bristol-Myers Research Laboratories (Wallingford, Conn.).

Compounds of Formula I

The synthesis of the hydroxymethylcyclopentenyl compounds of formulas 7a–18a and the hydroxymethylcyclopentyl compounds of formulas 7b–18b, from the versatile precursor, 1α-acetylamino-3α-acetoxymethylcyclopent-2-ene (1a) was accomplished as outlined in FIG. 1. Compound 1a was prepared as described in U.S. Pat. No. 4,138,562, the disclosure of which is incorporated by reference herein. Compound 2a was prepared from compound 1a by hydrolysis in the presence of a mild base, such as an alkaline earth metal hydroxide. To afford the pyrimidine compound 3a, compound 2a was reacted with an excess of 5-amino-4,6-dichloropyrimidine in the presence of an amine base, such as a trialkylamine, in an alcoholic solvent. Likewise, the cyclopentanyl compound 1b, which is obtained from compound 1a by hydrogenation, is hydrolyzed and reacted with 5-amino-4,6-dichloropyrimidine to yield the pyrimidinylcyclopentyl carbinol, 3b. Also, 2-amino-4,6-dichloropyrimidine was reacted with compound 2a to yield compound 4a, and with compound 2b to yield compound 4b.

Para-chloroaniline was diazotized with acidic sodium nitrite and reacted with compounds 4a and 4b to yield the chlorophenylazo intermediates 5a and 5b, respectively. Reduction of the azo intermediate 5a and 5b to yield 6a and 6b, respectively, was accomplished with zinc and acetic acid. See Shealy and Clayton, *J. Pharm. Sci.*, 62, 1433 (1973).

The 5-amino-6-chloro-4-pyrimidinyl intermediates 3a and 3b were converted to the 9-substituted-6-chloropurines 7a and 7b, respectively, by ring closure with triethylorthoformate and subsequent mild acid hydrolysis to remove ethoxymethylidenes and formates formed during the reaction. In like manner, the 2,5-diamino-6-chloro-4-pyrimidinyl intermediates 6a and 6b were ring-closed to the corresponding 2-amino-6-chloro-9H-purin-9-yl compounds 13a and 13b.

The 6-chloropurines 7a, 7b, 13a, and 13b were converted to the corresponding 6-hydroxy purines 8a, 8b, 14a and 14b, respectively, with aqueous base, i.e., by refluxing them with an alkali metal hydroxide such as NaOH. Chloro compounds 7a, 7b, 13a, 13b, 16a, and 16b were converted to the corresponding amino compounds 9a, 9b, 15a, 15b, 18a, and 18b, by reaction with liquid ammonia under pressure.

Mono- or di-substituted 6-amino compounds of formula I, wherein X is NR$_2$ and R=R=(lower)alkyl, phenyl or mixtures thereof with H, can be prepared by conventional methods for the conversion of halides to secondary or tertiary amines. For example, see I. T. Harrison et al., *Compendium of Organic Synthetic Methods*, Wiley-Interscience, N.Y. (1971) at pages 250–252. The 6-chloro substituent in compounds 7a, 7b, 13a, 13b, 16a, and 16b can be replaced with other halogen atoms by the use of various p-(halo)benzene diazonium chlorides in the conversion of 4a to 5a or of 4b to 5b, or by conventional methods of halide-halide exchange.

These conversions are extensively described in the context of purine nucleoside synthesis in *Nucleoside Analogs-Chemistry, Biology and Medical Applications*, R. T. Walker et al., eds., Plenum Press, N.Y. (1979) at pages 193–223, the disclosure of which is incorporated by reference herein.

Treatment of 7a and 7b with thiourea in refluxing alcohol, followed by alkaline hydrolysis afforded thiols 10a and 10b, respectively. See L. F. Fieser et al., *Reagents for Organic Synthesis*, John Wiley and Sons, Inc., N.Y. (1967) at pages 1165–1167 and U.S. Pat. No. 4,383,114, the disclosures of which are incorporated by reference herein. Phenyl or alkylthio-derivatives can be prepared from the corresponding thiols by the procedure of U.S. Pat. No. 4,383,114 (Example 6).

Ring closure of 3a and 3b with acidic aqueous sodium nitrate followed by neutralization with aqueous base directly afforded the corresponding 7-hydroxy-3H-1,2,3-triazolo[4,5d]pyrimidin-3-yl compound 11a and 11b, respectively. Ring closure of 6a and 6b afforded the corresponding 5-amino-7-chloro-3H-1,2,3-triazo[4,5d]pyrimidin-3-yl compounds 16a and 16b, respectively, which was hydrolyzed to the corresponding 7-hydroxy compounds 17a and 17b with aqueous NaOH. Compound 3a was converted to the corresponding 7-amino compounds 12a by reaction with acidic sodium nitrite, followed by reaction of the crude product with liquid ammonia. The 7-aminocyclopentyl carbinol 12b was prepared by hydrogenating 12a (Pd—C). Compounds of formula I, wherein Z is OH, X is NH$_2$ or OH, and Y is CH can be prepared from compounds 14a, 14b, 15a or 15b by deamination of the 2-amino group with nitrous acid, employing the procedure used by Davoll to convert 2-aminoadenosine to isoguanosine. See J. Davoll, *J. Amer. Chem. Soc.*, 73, 3174 (1951), the disclosure of which is incorporated by reference herein.

Compounds of formula I, wherein X is H, Z is NH$_2$ and Y is CH can be prepared from compounds 7a, 7b, 13a, or 13b by dehalogenation with zinc/water [J. R. Marshall et al., *J. Chem. Soc.*, 1004 (1951)] or by photolysis in dry nitrogen-purged tetrahydrofuran containing 10% triethylamine in a Rayonet photochemical reactor (2537A) by the method of V. Nair et al., *J. Org. Chem.*, 52, 1344 (1987).

Pharmaceutically-acceptable acid salts of compounds 7–18, as well as of AZT, ribavirin, CS-87 and d4T can be prepared as described in U.S. Pat. No. 4,383,114, the disclosure of which is incorporated by reference herein.

The invention will be further described by reference to the following detailed examples wherein elemental analyses were performed by M-H-W Laboratories, Phoenix, Ariz. Melting points were determined on a Mel-Temp apparatus and are corrected. Nuclear magnetic resonance spectra were obtained on Jeol FX 90QFT or Nicollet NT300 spectrometers and were recorded in DMSO-D$_6$. Chemical shifts are expressed in ppm downfield from Me$_4$Si. IR spectra were determined as KBr pellets with a Nicollet 50XC FT-IR spectrometer, and UV spectra were determined on a Beckmann DU-8 spectrophotometer. Mass spectra were obtained with an AEI Scientific Apparatus Limited MS-30 mass spectrometer. Thin layer chromatography (TLC) was performed on 0.25 mm layers of Merck silica gel 60F-254 and column chromatography on Merck 60 silica gel (230–400 mesh). All chemicals and solvents are reagent grade unless otherwise specified.

EXAMPLE 1

(±)-(1α,4α)-4-[(5-Amino-6-chloro-4-pyrimidinyl)-amino]-2-cyclopentenylcarbinol (3a)

A mixture of 1a (3.0 g, 15 mmol) and aqueous barium hydroxide (0.5N, 300 ml) was refluxed overnight. After cooling, it was neutralized with dry ice. The precipitate was filtered out, and the aqueous solution was concentrated to dryness. The residue was extracted with absolute ethanol and concentrated again to yield 2a as a colorless syrup 1.6 g (14 mmol).

To this syrup, 5-amino-4,6-dichloropyrimidine (4.59 g, 28 mmol), triethylamine (4.2 g, 42 mmol), and n-butanol (50 ml) were added and the mixture was refluxed for 24 hr. The volatile solvents were removed, the residue was absorbed on silica gel (7 g), packed in a flash column (4.0×12 cm) and eluted with $CHCl_3$—MeOH (20:1) to yield 2.69 g (74%) of compound 3a; mp 130°-132° C. An analytical sample was obtained by recrystalization from ethyl acetate (EtOAc), mp 134°-135° C., MS (30 ev, 200° C.); m/e 240 and 242 (M+ and M++2), 209 (M+·31), 144 (B+); IR: 3600-2600 (OH), 1620,1580 (C=C, C=N); Anal. ($C_{10}H_{13}ClN_4O$) C,H,N.

EXAMPLE 2

(±)-(1α,4α)-4-[(2-Amino-6-chloro-4-pyrimidinyl)-amino]-2-cyclopentenylcarbinol (4a)

To 14 mmol of crude 2a, 2-amino-4,6-dichloropyrimidine (3.74 g, 22.8 mmol), triethylamine (15 ml) and n-butanol (75 ml) were added and the mixture was refluxed for 48 hr. The volatile solvents were removed, residue was treated with methanol to separate the undissolved byproduct (the double pyrimidine nucleoside). The methanol solution was absorbed on silica gel (8 g) packed into a column (4.0×14 cm) and eluted with $CHCl_3$—MeOH (40:1) to yield 1.52 g (42%) of crude 4a. The product was recrystalized from ethyl acetate to yield 4a: mp 132°-134° C., MS (30 ev, 200° C.); m/e 240 and 242 (M+ and M++2), 209 (M+·31), 144 (B+); IR: 3600-3000 ($NH_2$, OH), 1620, 1580 (C=C, C=N); Anal. ($C_{10}H_{13}ClN_4O$) C,H,N.

EXAMPLE 3

(±)-(1α,4α)-4-{[2-Amino-6-chloro-5-(4-chlorophenyl)-azo]-4-pyrimidinyl]-amino}-2-cyclopentenylcarbinol (5a)

A cold diazonium salt solution was prepared from p-chloroaniline (1.47 g, 11.5 mmol) in 3N HCl (25 ml) and sodium nitrite (870 mg, 12.5 mmol) in water (10 ml). This solution was added to a mixture of 4a (2.40 g, 10 mmol), acetic acid (50 ml), water (50 ml) and sodium acetate trihydrate (20 g). The reaction mixture was stirred overnight at room temperature. The yellow precipitate was filtered and washed with cold water until neutral, then it was air-dried in the fumehood to yield 3.60 g (94%), of 5a, mp 229° C. (dec). The analytical sample was obtained from acetone-methanol (1:2), mp 241°-243° C. (dec). MS (30 ev, 260° C.): m/e 378 and 380 (M+ and M++2), 282 (B+); IR: 3600-3000 ($NH_2$, OH), 1620,1580 (C=C, C=N); Anal. ($C_{16}H_{16}Cl_2N_6O$) C,H,N.

EXAMPLE 4

(±)-(1α,4α)-4-[(2,5-Diamino-6-chloro-4-pyrimidinylamino]-2 cyclopentenylcarbinol (6a)

A mixture of 5a (379 mg, 1 mmol), zinc dust (0.65 g, 10 mmol), acetic acid (0.32 ml), water (15 ml) and ethanol (15 ml) was refluxed under nitrogen for 3 hr. The zinc was removed and the solvents were evaporated. The residue was absorbed on silica gel (2 g), packed into a column (2.0×18 cm), and eluted with $CHCl_3$—MeOH (15:1). A pink syrup was obtained. Further purification from methanol-ether yielded 6a as pink crystals, 170 mg (66%), mp 168°-170° C., MS (30 ev, 220° C.); m/e 255 and 257 (M+ and M++2), 224 (M+·31), 159 (B+); IR: 3600-3000 ($NH_2$, OH), 1620,1580 (C=C, C=N); Anal. ($C_{10}H_{14}ClN_5O$) C,H,N.

EXAMPLE 5

(±)-(1α,4α)-4-(6-chloro-9H-purin-9-yl)-2-cyclopentenylcarbinol (7a)

A mixture of 3a (1.30 g, 5.4 mmol), triethyl orthoformate (30 ml) and hydrochloric acid (12N, 0.50 ml) was stirred overnight at room temperature. The solvent was evaporated at 35° C. in vacuo. To the residue was added aqueous hydrochloric acid (0.5N, 30 ml) and the mixture was stirred for 1 hr. The mixture was neutralized to pH 7—8 with 1N sodium hydroxide and absorbed onto silica gel (8 g), packed in a column (4.0×8 cm), and eluted with $CHCl_3$—MeOH (20:1) to yield white crystals of 7a, 1.12 g (82%). The crude product was recrystalized from ethyl acetate to yield 7a, mp 108°-110° C., MS (30 ev, 200° C.); m/e 250 and 252 (M+ and M++2), 219 (M+·31), 154 (B+); IR: 3600-2800 (OH), 1600 (C=C, C=N); Anal. ($C_{11}H_{11}ClN_4O$) C,H,N.

EXAMPLE 6

(±)-(1α,4α)-4-(6-Hydroxy-9H-purin-9-yl)-2-cyclopentenylcarbinol (8a)

A mixture of 7a (251 mg, 1 mmol) and aqueous sodium hydroxide (0.2N, 10 ml) was refluxed for 3 hr. After cooling, the reaction mixture was adjusted to pH 5-6 with acetic acid. The reaction mixture was absorbed on silica gel (2 g) packed in a column (2.0×11 cm) and eluted with $CHCl_3$—MeOH (10:1) to yield 105 mg (45%) of 8a. The crude white product was recrystalized from water-methanol (3:1) to yield 8a, mp 248°-250° C. (dec), MS (30 ev, 300° C.); m/e 232 (M+), 214 (M+·18), 136 (B+); IR; 3600-2600 (OH), 1680,1600 (C=O, C=C, C=N); Anal. ($C_{11}H_{12}N_4O_2$) C,H,N.

EXAMPLE 7

(±)-(1α,4α)-4-(6-Amino-9H-purin-9-yl)1-2-cyclopentenylcarbinol (9a)

Liquid ammonia was passed into a bomb containing a solution of 7a (250 mg, 1 mmol) in methanol (5 ml) at −80° C. The bomb was sealed and heated at 60° C. for 24 hr. Ammonia and methanol were evaporated and the residue was recrystalized from water to yield off-white crystals of 9a, 187 mg (81%), mp 198°-200° C., MS (30 ev, 210° C.): m/e 231 ($M^{30}$), 213 (M+·18), 135 (B+); IR: 3600-2600 ($NH_2$, OH), 1700,1600 (C=C, C=N); Anal. ($C_{11}H_{13}N_5O$) C,H,N.

EXAMPLE 8

(±)-(1α,4α)-4-(6-Mercapto-9H-purin-9-yl)-2-cyclopentenylcarbinol (10a)

A mixture of 7a (125 mg, 0.5 mmol), thiourea (40 mg, 0.64 mmol) and n-propanol (5 ml) was refluxed for 2 hr. After cooling, the precipitate was isolated by filtration, washed with n-propanol, and dissolved in sodium hydroxide (1N, 5 ml). The solution was adjusted to pH 5 with acetic acid. The crude 10a (90 mg, 73%) was isolated again, mp 260°-262° C. (dec) and was recrystalized from N,N-dimethylformamide, to yield 10a, mp 263°-265° C. (dec). MS (30 ev, 290° C.): m/e 248 (M+), 230 (M+·18), 152 (B+); IR: 3600-3200 (OH), 3100,2400 (SH), 1600 (C=C, C=N); Anal. ($C_{11}H_{12}N_4OS$) C,H,N.

EXAMPLE 9

(±)-(1α,4α)-4-(2-Amino-6-chloro-9H-purin-9-yl)-2-cyclopentenyl carbinol (13a)

A mixture of 6a (1.41 g, 5.5 mmol) triethyl orthoformate (30 ml) and hydrochloric acid (12N, 1.40 ml) was stirred overnight. The suspension was dried in vacuo. Diluted hydrochloric acid (0.5N, 40 ml) was added and the mixture was reacted at room temperature for 1 hr. The mixture was neutralized to pH 8 with 1N sodium hydroxide and absorbed on silica gel (7.5 g) packed in a column (4.0×10 cm) and eluted by $CHCl_3$—MeOH (20:1) to yield off-white crystals of 13a, 1.18 g (80%). The crude product was recrystalized from ethanol to yield 13a, mp 145°-147° C. MS (30 ev, 220° C.): m/e 265 and 267 ($M^+$ and $M^++2$), 235 ($M^+$-30), 169 ($B^+$); IR: 3600-2600 ($NH_2$, OH), 1620,1580 (C=C, C=N); Anal. ($C_{11}H_{12}N_5OCl.\frac{1}{4} H_2O$) C,H,N.

EXAMPLE 10

(±)-(1α,4α)-4-(2-Amino-6-hydroxy-9H-purin-9-yl)-2-cyclopentenyl carbinol (14a)

A mixture of 13a (266 mg, 1 mmol) and aqueous sodium hydroxide (0.33N) was refluxed for 5 hr., absorbed onto silica gel (2 g) packed in a column (2.0×7.5 cm) and eluted with $CHCl_3$—MeOH (5:1). The crude product was recrystalized from methanol-water (1:4) to yield white crystals of 14a, 152 mg (61%), mp 254°-256° C. (dec). MS (30 ev, 200° C.): m/e 247 ($M^+$), 217 ($M^+$-30), 151 ($B^+$); IR: 3600-2600 ($NH_2$, OH), 1700, 1600 (C=O, C=C, C=N); Anal. ($C_{11}H_{13}N_5O_2.\frac{3}{4} H_2$) C,H,N.

EXAMPLE 11

(±)-(1α,4α)-4-(2,6-Diamino-9H-purin-9-yl)-2-cyclopentenylcarbinol (15a)

Liquid ammonia was passed into a solution of 13a (265 mg, 1 mmol) in methanol (10 ml) at −80° C. in a bomb. The bomb was sealed and heated at 75° C. for 48 hr. Ammonia and methanol were evaporated. The residue was absorbed on silica gel (2 g), packed in a column (2.0×10 cm) and eluted with $CHCl_3$—MeOH (15:1). The crude product was recrystalized from ethanol to yield 196 mg (80%) of 15a, mp 152°-155° C. MS (30 ev, 200° C.): m/e 246 ($M^+$), 229 ($M^+$-17), 216 ($M^+$-30), 150 ($B^+$); IR: 3600-3000 ($NH_2$, OH), 1700,1650-1600 (C=O, C=C, C=N); Anal. ($C_{11}H_{14}N_6O$) C,H,N.

EXAMPLE 12

Esterification of Compound 14a (1α,4α)-4-(2-Amino-6-hydroxy-9H-purin-9-yl)-2-cyclopentenyl Acetoxycarbinol To a suspension of 14a (130 mg, 0.50 mmol) and 4-dimethylaminopyridine (5 mg, 0.04 mmol) in a mixture of acetonitrile (6 ml) and triethylamine (0.09 ml, 0.66 mmol) was added acetic anhydride (0.06 ml, 0.6 mmole). The mixture was stirred at room temperature for 3 hr. Methanol (1 ml) was added to quench the reaction. The solution was concentrated and absorbed on silica gel (1.5 g), packed on a column (2.0×12 cm), and eluted with $CHCl_3$—MeOH (20:1). The product fractions were collected and concentrated to yield a white solid. The solid product was washed with MeOH—AcOEt to yield 123 mg of the purified acetoxycarbinol (85%). Further purification from methanol afforded needlelike crystals, mp 237°-239° C.; Anal. ($C_{13}H_{15}N_5O_3$) C,H,N.

EXAMPLE 13

(1S,4R)-4-(2-Amino-6-hydroxy-9H-Purin-9-yl)-2-cyclopentenyl Carbinol ((−)14a)

The diamino analog, 15a, (100 mg) was dissolved in 3 ml of 0.05M $K_2PO_4$ buffer (pH 7.4) at 50° C. The solution was cooled at 25° C. and 40 units of adenosine deaminase (Sigma, Type VI, calf intestinal mucosa) was added. After three days of incubation at room temperature, a precipitate formed and was removed by filtration to yield 18.2 mg of crude product. The filtrate was concentrated to 1.5 ml and refrigerated for 2 days. Additional solid (26.8 mg) was obtained by filtration. The two solid fractions were recrystalized from water to yield the pure product, mp 269°-272° C.; $[\alpha]_D^{24} - 62.1$ (c 0.3 MeOH).

EXAMPLE 14

(1R' 4S)-4-(2-Amino-6-hydroxy-9H-purin-9-yl)-2-cyclopentenyl carbinol ((+)14a)

The filtrates from the preparation of the 1S,4R isomer were combined and evaporated to dryness. The unchanged diamino starting material was separated on a silica gel flash column using 10% methanol/chloroform. The diamino compound was dissolved in 0.05M $K_2PO_4$ buffer, pH 7.4 (15 ml) and 800 units of adenosine deaminase was added. The solution was incubated for 96 hr at 37° C. TLC indicated some unreacted product remained. The solution was heated in boiling water for 3 min and filtered to remove denatured protein. Another 800 units of adenosine deaminase was added and the processes were repeated. The deproteinated solution was evaporated to dryness and the product was crystallized from water to yield a white solid; mp 265°-270° C.; $[\alpha]_D^{24} + 61.1$ (c 0.3MeOH).

EXAMPLE 15

Cytotoxicity Assay

The $ED_{50}$ cytotoxicity concentrations determined for analogs 7a, 9a, 10a, 16a, and 17a in the P-388 mouse leukemia cell culture assay are given in Table II.

TABLE II

| Inhibitory Concentrations of Carbocyclic Nucleosides for P-388 Leukemia Cells in Cultures* | |
|---|---|
| Compound | $ED_{50}$, μg/ml |
| 7a | 12.0 |
| 9a | 40.0 |
| 10a | 3.0 |
| 16a | 1.0 |
| 17a | 4.5 |

*Assay Technique: R. G. Almquist and R. Vince, J. Med. Chem., 16, 1396 (1973).

Therefore, all of the compounds listed on Table II are active against P-388 mouse leukemia.

EXAMPLE 16

Anti-HIV Assay

Compound 14a was screened for anti-HIV activity at the National Cancer Institute, Frederick Cancer Research Facility, Frederick, Md. (FCRF). The screening mode operational procedures utilized at FCRF are set forth in detail in U.S. patent application Ser. No.

07/146,252, filed Jan. 20, 1988, the disclosure of which is incorporated by reference herein.

Figure 2:
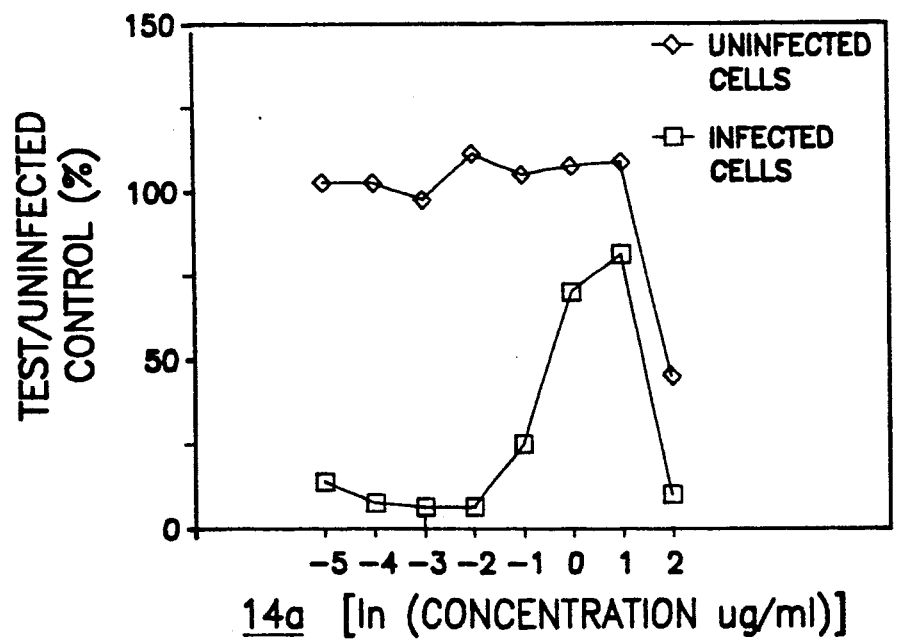
FIG. 2 is a graphic depiction of cells exposed to 14a/control cells (%) plotted vs. concentration of 14a for both uninfected cells and cells infected with HIV.
Figure 3:
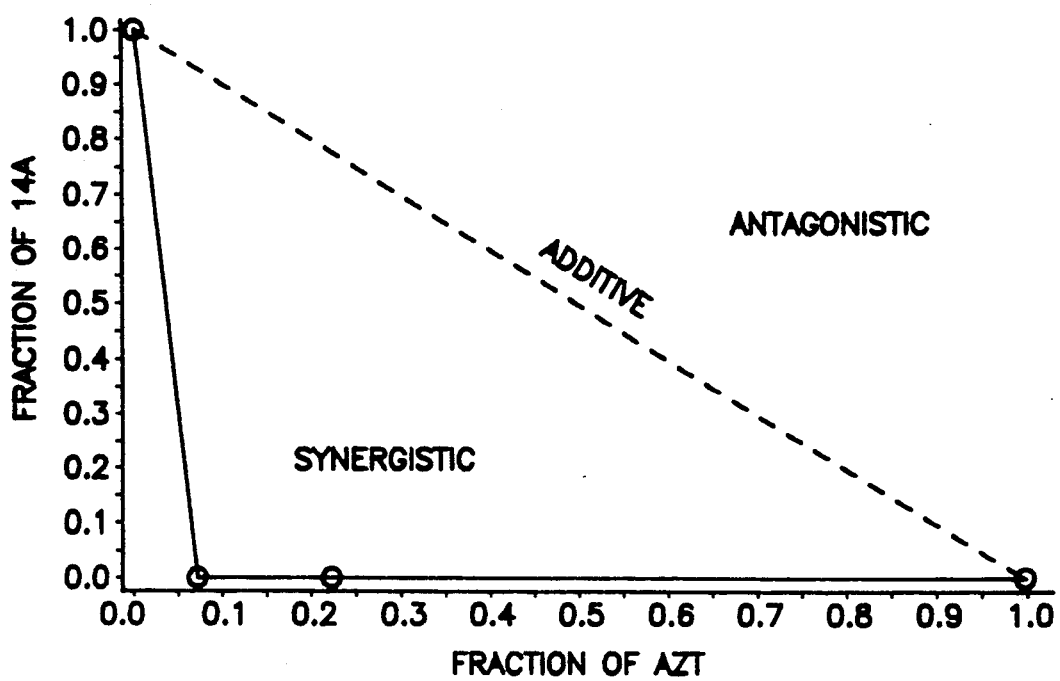
FIG. 3 is an isobologram depicting 25% inhibition of HIV replication in CEM cells by compound 14a, ribavirin and combinations thereof.
Figure 4:
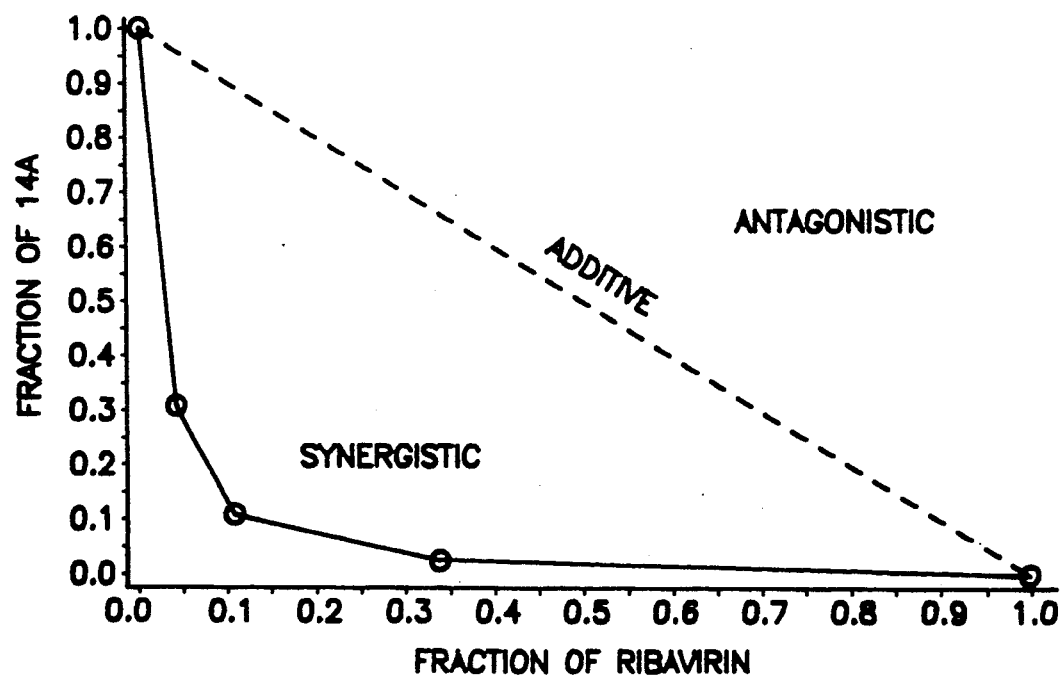
FIG. 4 is an isobologram depicting 40% inhibition of HIV replication in MT2 cells by compound 14a, AZT and combinations thereof.
Figure 5:
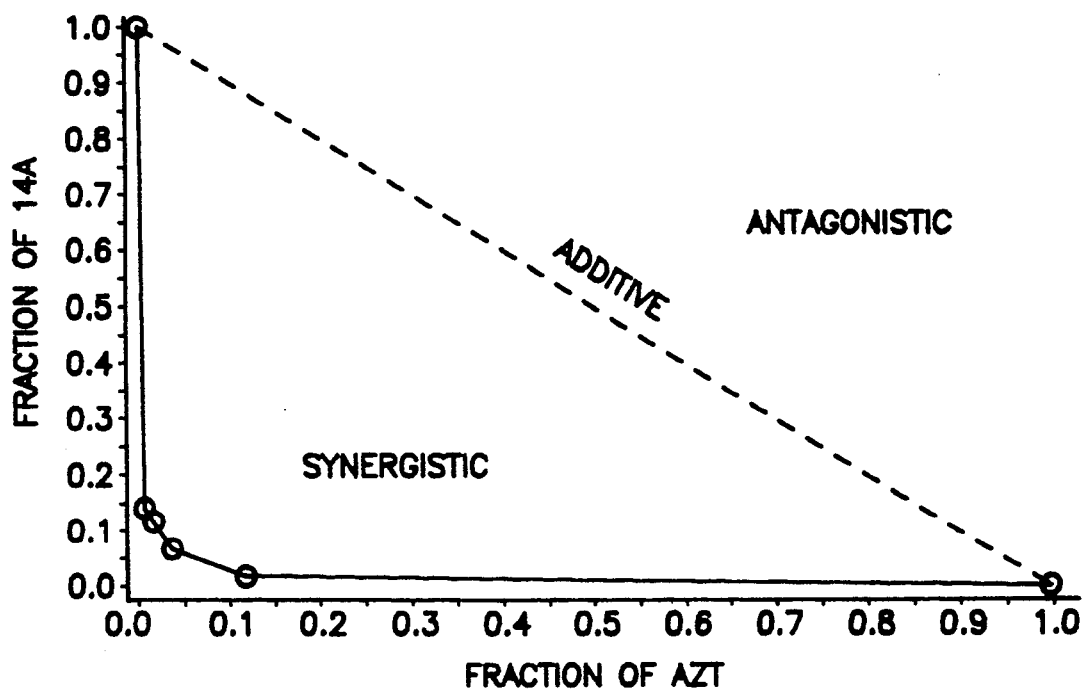
FIG. 5 is an isobologram depicting 50% inhibition of HIV replication in MT2 cells by compound 14a, AZT and combinations thereof.

FIG. 2 depicts a plot of the percentage of test cells over uninfected cells (%) for both infected and uninfected cells as a function of the increasing concentration of compound 14a.

The data plotted on FIG. 2 permit the calculation of an effective concentration ($EC_{50}$) with respect to infected cells of about 0.15 μg/ml, an inhibitory concentration ($IC_{50}$) with respect to normal cells of about 100 μg/ml, and a therapeutic index ($TI_{50}$) of about 667. An earlier assay carried out at the Southern Research Institute yielded a $TI_{50}$ of about 200 when MT-2 cells were cultured with H9/HTLV-IIIB.

The activity of compounds 7a, 9a, 10a, 13a, 14a, (−)14a, and 15a against HIV are given on Table III, below.

TABLE III

| Compound | $ED_{50}$ | $ID_{50}$ | $ID_{50}$ | Cell Line |
|---|---|---|---|---|
| 7a | — | 58.5 | — | MT-2 |
| 9a | 2.3 | 50 | 21.4 | MT-2 |
| 10a | — | 7.33 | — | MT-2 |
| 13a | 0.41 | 6.97 | 17.3 | MT-2 |
| (±)14a | 0.15 | 100 | 667 | MT-2 |
| (±)14a | 0.009 | 3.79 | 404 | MT-2 |
| (±)14a | 0.35 | 39.9 | 112 | MT-2 |
| (±)14a | 0.20 | 55.3 | 272 | ATH-8 |
| (−)14a | 1.95 | >250 | >128 | CEM-C |
| (−)14a | 0.325 | 135 | 416 | MT-2C |
| (−)14a | 0.665 | 189 | 284 | CEM-C |
| 15a | 1.9 | >125 | 66 | MT-2C |
| 15a | 2.92 | >125 | 42.7 | MT-2C |

Compound 14a was also found to be active against feline leukemia virus ($ED_{50}=1.9$; FAIDS variant); murine leukemia virus ($ED_{50}=1.1$; Cas—BR—M type) and simian AIDS virus ($ED_{50}=2.8$; D/Washington type).

EXAMPLE 17

Antiviral Synergy Studies with Compound 14a plus 3'-Azido-3-Deoxythymidine (AZT), ddI, Ribavirin, CS-87 or d4T 1. Introduction The methods and procedures used for determining the combined antiviral effects of 14a with AZT, ribavirin, ddI, CS-87 and d4T are presented here in two parts. The first part consists of the method for performing the antiviral assay. The second part describes the method for performing the assay with two compounds in combination. The protocol for the first part is presented below in "Large Scale Screening Procedure: Preinfection Protocol." The second part is described below in "Procedures for Combined Drug Assay".

2. Large Scale HIV Screening Procedure: Preinfection Protocol

The following are the current screening mode operational procedures utilized at Southern Research Institute, Birmingham, Ala. The procedure consists of 3 operations: 1) preparation of infected cells and distribution of the test plates; 2) preparation of drug dilution plates and distribution to the test plates; and 3) XTT assay procedure.

A. Infection and Distribution of Cells to Microtiter Trays

Cells to be treated in 50 ml conical centrifuge tubes for 30 minutes with 1-2 μg/ml of polybrene at 37° C., and pelleted (8 min., 1200 RPM). Virus is added [in RMPI-1640, 10% fetal calf serum (FCS), with interleukin-2 (IL-2) (for ATH8 cells), and antibiotics] to provide an MOI of approximately 0.01. An MOI of 0.01 is obtained by adding $10^3$ infectious units of virus to $10^5$ cells. Medium alone is added to virus-free control cells. The treated or control cells are incubated for 1 hour at 37° C. in 5% $CO_2$ in air. Infected or uninfected cells are diluted to give $1 \times 10^4$ cells/100 μl ($2 \times 10^4$ cells/100 μl for ATH8 cells). Infected or uninfected cells (100 μl) are distributed to appropriate wells of a 96 well, U-bottom, microtiter plate. Each compound dilution is tested in duplicate with infected cells. Uninfected cells are examined for drug sensitivity in a single well for each dilution of compound. Drug free control cells, infected and uninfected, are run in triplicate in wells B3 through D3 and E3 through G3, respectively. Wells A4 through A11 and H4 through H11 are drug blanks and get medium alone at this point. The plates are then incubated at 37° C. in 5% $CO_2$ until ready for drug addition.

B. Drug Dilution and Addition

The first dilution of each drug is made in a test tube according to the dilution specified hereinbelow. The remaining dilutions are made in 96-well plates. All wells of each plate are filled with 225 μl of medium using a Cetus liquid handling system programed according to the plate filling worksheet. Twenty-five microliters (25 μl) of 2 diluted compounds are manually added to row 11 of a filled dilution plate in the same order in which the drugs will appear on the test plate. The two compounds are then serially diluted 10 fold from row 11 through row 4, using the Cetus liquid handling system, preprogramed with the serial dilution file worksheet.

Using a multi-channel pipettor with 6 microtips, 100 μl of each drug dilution is transferred to the test plate; 100 μl from wells A4 through H4 of the dilution plate to the same wells of the test plate. Wells B3 through G3 and B2 through G2 receive medium alone.

Test plates are incubated at 37° C. in 5% $CO_2$ in air for 7 days or until virus control cells are lysed as determined microscopically.

C. Quantitation of Viral Cytopathogenicity and Drug Activity by Microculture Tetrazolium Assay (MTA)

An XTT-PMS solution is prepared immediately prior to its addition to the wells of the culture dish [1 mg/ml XTT; 2,3-bis(2-methoxy-4-nitro-5-sulfophenyl)-5-(phenylamino)carbonyl-2H-tetrazolium hydroxide solution in media without FCS]. The stock PMS (phenazine methosulfate (15.3 mg PMS/ml FBS)) solution is diluted 1:100 (0.153 mg/ml). The diluted PMS (40 μl) was added to every ml of XTT required (this will give a final PMS concentration of 0.02 mM after addition to the plate). The XTT-PMS mixture (50 μl) is added to each of the appropriate wells. The plate is incubated for four hours at 37° C. The plate lids are removed and replaced with adhesive plate sealers (Dynatech cat#001-010-3501). The sealed plate is inverted, placed in the ELISA plate reader and read at 450 nm.

3. Procedures for Combined Drug Assay

The assay is conducted in 96-well cell culture plates. These plates have 12 wells across (numbered 1-12) and 8 wells down (lettered A-H). The selected concentrations of 14a or (−)14a were placed in the horizontal rows of wells, and the selected concentrations of AZT, ribavirin, CS-87, ddI or d4T were placed in the vertical rows. The following concentrations of 14a or (−)14a were used (μg/ml): 0.032, 0.1, 0.32, 1.0, 3.2, 10, and 32. The following concentrations of AZT, ribavirin, CS-87, ddI or d4T were used (μg/ml): 0.01, 0.032, 0.1, 0.32, 1.0, 3.2, 10, and 32.

The drugs were prepared at four times the above concentrations and were added to plates in the following manner: 0.05 ml of 14a or (−)14a concentrations were added to wells, using two wells per concentration across the plate. Next, 0.05 ml of AZT, ribavirin, CS-87, ddI or d4T concentrations were added to wells in vertical rows. Next, 0.1 ml of virus-infected cells was added to each well. The total volume in each well was therefore 0.2 ml, and the final concentration of each drug was 0.05/0.2 to yield the final concentrations.

The cells used were the MT2 or CEM cell lines. Virus-infected cells were prepared as described in Part 2, above. The cell culture medium was RPMI 1640 containing 10% (v/v) fetal calf serum as described in Part 2. The medium also contained penicillin (100 units/ml) and streptomycin (100 μg/ml).

Additional plates were included in the assay for assessment of toxicity, and were arranged as described above. Also included were plates containing each drug alone. Uninfected cells (cell controls) and virus-infected cells (virus controls) were included in each plate.

The plates were incubated for seven days at 37° C. in a humidified atmosphere of 5% $CO_2$ in air. The protocol of Part 2, above, was followed for the quantitation of viral cytopathogenicity and drug activity.

The data from the assays consists of optical density (O.D.) values for each well which are a measure of cell viability. The mean for each duplicate well group was divided by the mean for the cell control group (less background) to give the percent of the cell control. These values were used to statistically compare the protective effects of each drug alone with drug combination sets by isobologram analysis, as depicted in FIGS. 3–9.

4. Results

The clear significance of these combination antiviral data with 14a or (−)14a plus AZT, with 14a plus ribavirin, with (−)14a plus CS-87, and with (−)14a plus d4T is that greater antiviral activity is achieved with these synergistic combinations against the Human Immunodeficiency Virus (HIV) than with either of the drugs alone. Also, lower concentrations of these antiviral drugs in combination may be used to achieve efficacy in terms of inhibition of HIV-induced cytopathology which is similar to that obtained with much higher levels of the same drugs when they are used alone. Thus, reductions in the potential toxicity of the antiviral drugs and significant increases in the potential therapeutic value of these antiviral agents are achieved when they are used in combination rather than as single drugs alone. These observations should prove to have direct clinical usefulness in the improved treatment of patients with AIDS and AIDS-related complex (ARC) over current treatment modalities.

What is claimed is:

1. A pharmaceutical composition comprising an effective synergistic anti-HIV amount of a combination of (a) 3′-azido-3′-deoxythymidine, 2′,3′-dideoxy-2′,3′-didehydrothymidine (d4T), 3′-azido-2′,3′-dideoxyuridine (CS-87), or ribavirin and (b) a compound of the formula (I):

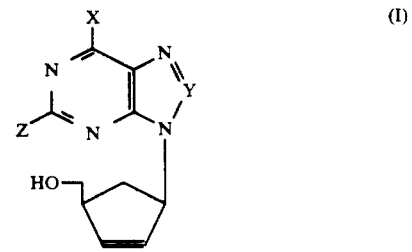

wherein X is H, $NRR^1$, SR, OR or halogen, Z is H, $OH^2$, or $NRR^1$, Y is CH; R, $R^1$ and $R^2$ may be the same or different, and are selected from the group consisting of H, $C_{1-4}$alkyl and aryl; and the pharmaceutically acceptable salts thereof.

2. The composition of claim 1 wherein X is Cl.

3. The composition of claim 1 wherein X is OH.

4. The composition of claim 1 wherein X is $NH_2$.

5. The composition of claim 4 wherein the compound of formula I is (1S,4R)-4-(2-amino-6-hydroxy-9H-purin-9-yl)-2-cyclopentenylcarbinol.

6. The composition of claim 1 which consists essentially of ribavirin and the compound of formula I.

7. The composition of claim 1 which consists essentially of 3′-azido-3′-deoxythymidine and the compound of formula I.

8. The composition of claim 1 which consists essentially of 2′,3′-dideoxy-2′,3′-didehydrothymidine and the compound of formula I.

9. The composition of claim 1 which consists essentially of 3′-azido-2′,3′-dideoxyuridine and the compound of formula I.

* * * * *

UNITED STATES PATENT AND TRADEMARK OFFICE
CERTIFICATE OF CORRECTION

PATENT NO. : 5,122,517
DATED : 06/16/92
INVENTOR(S) : Vince et al.

It is certified that error appears in the above-identified patent and that said Letters Patent is hereby corrected as shown below:

Column 1, line 3,
After the title, please insert the following paragraph:

--GRANT INFORMATION

This invention was made with Government support under Grant No. 5 R 01 CA23263, awarded by the National Institutes of Health. The Government has certain rights in this invention.--

Signed and Sealed this

Thirtieth Day of November, 1993

Attest:

BRUCE LEHMAN

*Attesting Officer*     *Commissioner of Patents and Trademarks*